United States Patent [19]

Kaneko, deceased et al.

[11] 4,032,573
[45] June 28, 1977

[54] ORTHO-ACYLATED ANILIDE DERIVATIVES AND SALTS THEREOF

[75] Inventors: Shinichi Kaneko, deceased, late of Kobe, Japan, by Michio Kaneko, legal representative; Tsuyoshi Kobayashi, Mino, Japan; Yoshiaki Takebayashi; Shigeho Inaba, both of Takarazuka, Japan; Hisao Yamamoto, Nishinomiya, Japan

[73] Assignee: Sumitomo Chemical Company, Limited, Osaka, Japan

[22] Filed: Feb. 19, 1976

[21] Appl. No.: 659,197

Related U.S. Application Data

[63] Continuation-in-part of Ser. No. 369,621, June 13, 1973, abandoned.

[52] U.S. Cl. .................... 260/562 N; 424/320
[51] Int. Cl.² ........................ C07C 103/50
[58] Field of Search ............ 260/561 A, 562 N

[56] References Cited

UNITED STATES PATENTS 3,455,985  7/1969  Sternbach et al. ............ 260/465
3,657,344  4/1972  Stempel et al. ............... 260/562 N

OTHER PUBLICATIONS

Tricerri et al., Chem. Abstracts, 50 (1956) col. 5990c.
Oelschlager, Arzneimittel Forschung, vol. 8, 1958, 532–535.

Primary Examiner—Arthur P. Demers
Attorney, Agent, or Firm—Sughrue, Rothwell, Mion, Zinn & Macpeak

[57] ABSTRACT

Ortho-acylated anilide derivatives represented by the formula:

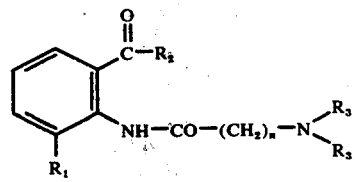

wherein $R_1$, $R_2$ and $R_3$ are each $C_{1-3}$ alkyl, and $n$ is 1 or 2, and salts thereof.

6 Claims, No Drawings

ORTHO-ACYLATED ANILIDE DERIVATIVES AND SALTS THEREOF

CROSS REFERENCE TO RELATED APPLICATION

This application is a continuation-in-part of our application Ser. No. 369,621, filed June 13, 1973, now abandoned, the benefit of which is claimed.

BACKGROUND OF THE INVENTION

1. Field of the Invention

The present invention relates to ortho-acylated anilide derivatives and salts thereof.

2. Description of the Prior Art

In the prior art meta acylated acet(and propion)anilides and para acylated acetanilides are known. See, e.g., S. Tricerri et al., C.A., 50, 5990 (1956), H. Oelschlager, Arzneimittel-Forsch, 8, 532-9 (1958).

SUMMARY OF THE INVENTION

One object of this invention is to provide novel ortho acylated anilide derivatives which are markedly and unexpectedly superior in both local anesthetic and anti-arrhythmic activity to the compounds of the prior art.

More particularly, the present invention relates to novel ortho-acylated anilide derivatives of formula (I):

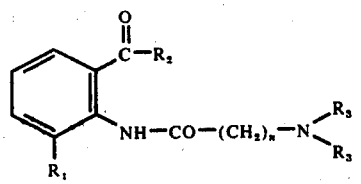

wherein $R_1$, $R_2$ and $R_3$ are each $C_1$—$_3$ alkyl; and $n$ is 1 or 2, and salts thereof, which are useful as local anesthetic, anti-arrhythmic and analgesic agents and which can be prepared from the corresponding aniline derivatives via a two step process.

DESCRIPTION OF PREFERRED EMBODIMENTS

In the above formula (I), examples of $C_1$—$_3$ alkyl groups are methyl, ethyl, n-propyl and isopropyl.

The anilide compounds of formula (I) can form acid addition salts, examples of which are hydrochloride, hydrobromide, acetate, oxalate, citrate, tartrate, succinate, fumarate, lactate, etc.

Among the compounds of formula (I), the following compounds of formula (II) are preferred:

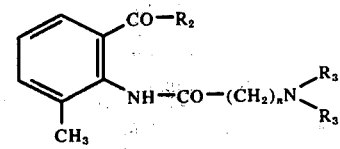

wherein $R_2$, $R_3$ and $n$ are as defined above, and the following compounds of formula (III) are mot preferred:

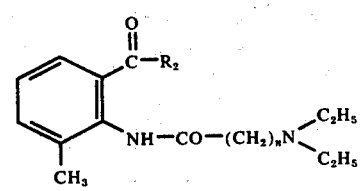

wherein $R_2$ and $n$ are as defined above.

The anilide derivatives of the above formulae and their pharmaceutically acceptable acid addition salts have excellent local anesthetic, anti-arrhythmic and analgesic activities and lower toxicity as compared to lidocaine.

The anilide derivatives of the above formulae can be prepared from the corresponding aniline derivatives through the two steps as shown in the following scheme:

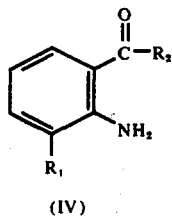 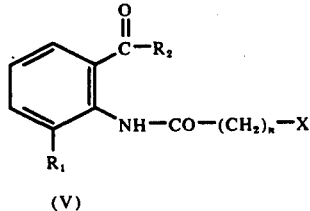

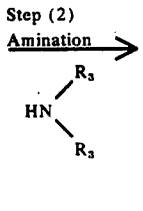 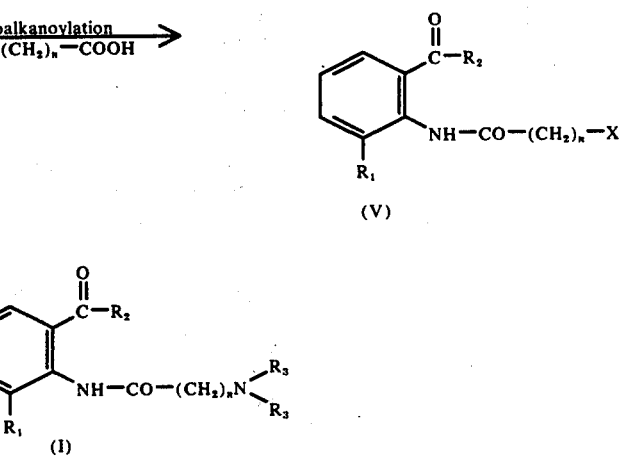

wherein X is halogen, and $R_1$, $R_2$, $R_3$ and $n$ are as defined above.

The reaction of step (1) above comprises a haloalkanoylation of the aniline derivative (IV), where the aniline derivative (IV) is reacted with a haloalkanoic acid of formula (VI):

$$X—(CH_2)_n—COOH \quad (VI)$$

wherein X and $n$ as defined above, or with a functional derivtive thereof such as an acid halide. The reaction of step (1) is preferably effected in the presence of a condensing agent such as sodium acetate, pyridine, etc., in an inert solvent such as ether, benzene, etc. The reaction proceeds at room temperature and, if desired, can be effected while heating or cooling.

The reaction of step (2) above comprises an amination of the haloalkanoylanilide derivative (V). The haloalkanoylanilide derivative (V) is reacted with an amine of the formula (VII)

wherein $R_3$ is as defined above. The reaction of step (2) can be conducted in the presence or absence of a condensing agent such as triethylamine, if desired, and in an inert solvent such as benzene, toluene, etc. The reaction can be effected at room temperature and atmospheric pressure or at elevated temperature and elevated pressure.

Anilide derivatives of the above formulae and their salts are therapeutically effective compounds which are useful as local anesthetics, anti-arrhythmic and analgesic agents. They may be administered orally or parenterally, in conventional dosage forms such as tablets, capsules, injections or the like, comprising 10 to 300 mg per kg of body weight of the compound, in combiation with a pharmaceutically acceptable carrier according to accepted pharmaceutical practice.

The starting aniline derivatives (IV) can be prepared, for example, by reacting an indole derivative with an oxidizing agent and hydrolyzing as shown by the following scheme:

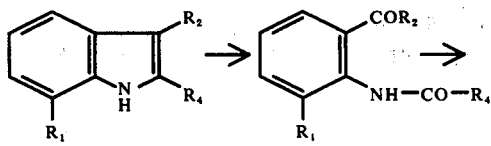

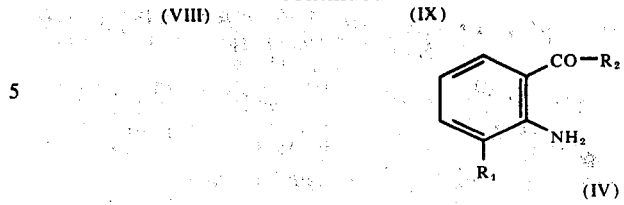

wherein $R_1$ and $R_2$ are as defined above, $R_4$ is hydrogen, $C_1$—$_3$ alkyl, aryl, alkoxycarbonyl, carbamoyl or cyano.

The following experiments compare the compounds of this invention with the compounds disclosed by Tricerri et al., in *Chemical Abstracts*, 50, 5990 (1956) and by Oelschlager in *Arzneimittel Forsch*, 8, 532 (1958), with respect to local anesthetic activity and anti-arrhythmic activity.

TEST METHODS

1. Local anesthetic activity

The local anesthetic activity of each of the compounds was determined in accordance with the method of Bulbring E. and Waida, *Journal Pharmacol. Exp. Ther.*, 85, 78 (1945).

2. Anti-arrhythmic activity

The anti-arrhythmic activity of each of the compounds was determined in accordance with the method of J. W. Lawson, *Journal Pharmacol. Exp. Ther.*, 160, 22 (1967).

RESULTS

The following results were obtained.

| Compounds of this invention | Local anesthetic activity in guinea pigs $ED_{50}$ intracutaneous injection W/V % | Anti-arrhythmic activity in mice $ED_{50}$ Intraperitoneal injection mg/kg |
|---|---|---|
| [structure: 2-COCH₃, 3-CH₃, NH—CO—CH₂CH₂N(C₂H₅)₂ · HCl] | 0.33 | 50 |
| [structure: 2-COCH₃, 3-CH₃, NH—CO—CH₂N(C₂H₅)₂ · HCl] | 0.12 | 80 |
| [structure: 2-CO—CH₂CH₂CH₃, 3-CH₃, NH—CO—CH₂CH₂N(C₂H₅COOH)₂] | 0.09 | 25 |
| Known compounds [H₃C—CO—C₆H₄—NH—CO—CH₂N(C₂H₅)₂ · HCl] (in Tricerri et al.) | 1.0 | 250 |

| Compounds of this invention | Local anesthetic activity in guinea pigs ED$_{50}$ intracutaneous injection W/V % | Anti-arrhythmic activity in mice ED$_{50}$ Intraperitoneal injection mg/kg |
|---|---|---|
| 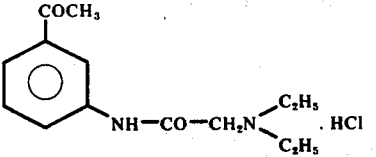 (in Oelschlager) | 1.0 | 180 |
| 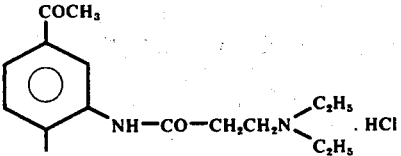 (in Oelschlager) | 1.48 | 97 |

Practical and presently preferred embodiments of the present invention are illustrated in the following Examples. [A] Haloalkanoylation

EXAMPLE 1

To a mixture of 4.8 g of 2-acetyl-6-methylaniline, 3 of sodium acetate and 120 ml of ether was simultaneously added a solution of 13.2 g of bromoacetyl bromide in 30 ml of ether and 60 g of ice at −3 to 0° C for 15 minutes. The resultant mixture was stirred at 0° to 5° C for 2 hours. The ether layer was separated, washed with an aqueous solution of sodium carbonte, dried over anhydrous sodium sulfate and evaporated to give 2-bromo-2'-acetyl-6'-methylacetanilide as crystals. m.p. 97° – 100° C.

Preparation of 2-acetyl-6-methylaniline

To a solution of 5.8 g of 2,3,7-trimethylindole in 180 ml of methanol was added dropwise a solution of 17 g of sodium metaperiodate in 180 ml of water at room temperature for 15 minutes. The resultant mixture was stirred at room temperature for 3 hours and extracted with dichloromethane. The extract was evaporated to dryness. Ether was added to the residue to give 2-acetyl-6-methylacetanilide as crystals.

A mixture of 6 g of 2-acetyl-6-methylacetanilide, 35 ml of conc. hydrochloric acid and 35 ml of ethanol was stirred under refluxing for 7 hours. The reaction mixture was concentrated, neutralized with aqueous ammonia and extracted with ether. The ether extract was washed with water, dried over anhydrous sodium sulfate and evaporated to give 2-acetyl-6-methylaniline as crystals.

EXAMPLE 2

In the same manner as in Example 1, but replacing 2-acetyl-6-methylaniline by 2-methyl-6-propionylaniline, there was obtained 2-bromo-2'-methyl-6'-propionylacetanilide.

EXAMPLE 3

In the same manner as in Example 1 but replacing 2-acetyl-6-methylaniline by 2-methyl-6-(2'-methylpropionyl)-aniline, there was obtained 2-bromo-2'-methyl-6'-(2''-methylpropionyl)acetanilide.

EXAMPLE 4

In the same manner as in Example 1 but replacing 2-acetyl-6-methylaniline by 2-methyl-6-n-butanoylaniline, there was obtained 2-bromo-2'-methyl-6-n-butanoylacetanilide.

EXAMPLE 5

In the same manner as in Example 1 but replacing bromoacetyl bromide by 3-bromopropionyl chloride, there was obtained 3-bromo-2'-acetyl-6'-methylpropionanilide. m.p. 99°–101° C.

EXAMPLE 6

In the same manner as in Example 1 but replacing 2-acetyl-6-methylaniline and bromacetyl bromide by 2-methyl-6-propionylaniline and 3-bromopropionyl chloride, there was obtained 3-bromo-2'-methyl-6'-propionylpropionanilide.

EXAMPLE 7

In the same manner as in Example 1 but replacing 2-acetyl-6-methylaniline and bromoacetyl bromide by 2-methyl-6-n-butanoylaniline and 3-bromopropionyl chloride, there was obtained 3-bromo-2'-methyl-6'-n-butanoylpropionanilide. [B] Amination.

EXAMPLE 1

To a solution of 4.0 g of 2-bromo-2'-acetyl-6'-methylacetanilide in 60 ml of toluene was added 2.5 g of diethylamine at room temperature. The resultant mixture was stirred at room temperature overnight. The reaction mixture was washed with water, dried over anhydrous sodium sulfate and evaporated to give an oily residue. The residue was dissolved in ether and hydrogen chloride was added to the solution to give crystals. Recrystallization from ethanol-ether gave 2-(diethylamino)-2'-acetyl-6'-methylacetanilide hydrochloride having a melting point of 141 to 143° C.

EXAMPLE 2

To a solution of 1.5 g of 3-bromo-2'-acetyl-6'-methylpropionanilide in 20 ml of benzene was added 0.8 g of diethylamine at room temperature. The resultant mixture was stirred at room temperature for 24 hours. The reaction mixture was washed with water, dried over anhydrous sodium sulfate and evaporated to give an oily residue. The residue was dissolved in ether and hydrogen chloride was added to the solution to give crystals. Recrystallization from ethanol gave 3-(diethylamino)-2'-acetyl-6'-methylpropionanilide hydrochloride having a melting point of 124° to 126° C.

EXAMPLE 3

In the same manner as in Example 1 but replacing 2-bromo-2'-acetyl-6'-methylacetanilide by 2-bromo-2'-methyl-6'-propionylacetaniide, there was obtained 2-(diethylamino)-2'-methyl-6'-propionylacetanildie hydrochloride having a melting point of 145 to 146° C.

EXAMPLE 4

In the same manner as in Example 1 but replacing 2-bromo-2'-acetyl-6'-methylacetanilide by 2-bromo-2'-methyl-6'-(2''-methylpropionyl)acetanilide, there was obtained 2-(diethylamino)-2'-methyl-6'-(2''-methylpropionyl)acetanilide hydrochloride having a melting point of 102 to 104° C.

EXAMPLE 5

In the same manner as in Example 1 but replacing 2-bromo-2'-acetyl-6'-methylacetanilide by 2-bromo-2'-methyl-6'-n-butanoylacetanilide, there was obtained 2-(diethylamino)-2'-methyl-6'-n-butanoylacetanilide hydrochloride having a melting point of 121° to 123° C.

EXAMPLE 6

In the same manner as in Example 2 but replacing 3-bromo-2'-acetyl-6'-methylpropionanilide by 3-bromo-2'-methyl-6'-n-butanoylpropionanilide, there was obtained 3-(diethylamino)-2'-methyl-6'-n-butanoylpropionanilide hydrochloride.

EXAMPLE 7

In the same manner as in Example 2 but by replacing 3-bromo-2'-acetyl-6'-methylpropionanilide and hydrogen chloride with 3-bromo-2'-methyl-6'-n-butanoylpropionanilide and oxalic acid, respectively, there was obtained 3-(diethylamino)-2'-methyl-6'-n-butanoylpropionanilide oxalate having a melting point of 110 to 112° C.

While the invention has been described in detail and with reference to specific embodiments thereof, it will be apparent to one skilled in the art that various changes and modifications can be made therein without deparing from the spirit and scope thereof.

What is claimed is:

1. An anilide compound of the formula:

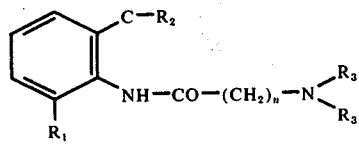

wherein $R_1$, $R_2$ and $R_3$ are each $C_1$ - $_3$ alkyl; and n is 1 or 2, and the non-toxic salts thereof.

2. A compound of the formula:

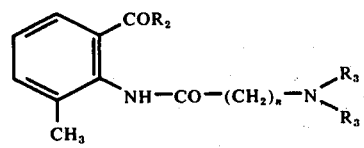

wherein $R_2$ and $R_3$ are each $C_1$ - $_3$ alkyl; and n is 1 or 2, and the non-toxic salts thereof.

3. A compound of the formula:

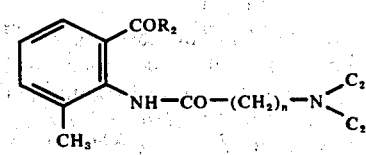

wherein $R_2$ is $C_1$ - $_3$ alkyl, n is 1 or 2, and the non-toxic salts thereof.

4. 3-(Diethylamino)-2'-acetyl-6'-methylpropionanilide hydrochloride.

5. 2-(Diethylamino)-2'-n-butanoyl-6'-methylacetanilide hydrochloride.

6. 3-(Diethylamino)-2'-n-butanoyl-6'-methylpropionanilide oxalate.

* * * * *